United States Patent
Noda et al.

(10) Patent No.: US 10,198,630 B2
(45) Date of Patent: Feb. 5, 2019

(54) PEAK DETECTION METHOD

(71) Applicant: SHIMADZU CORPORATION, Kyoto-shi, Kyoto (JP)

(72) Inventors: Akira Noda, Nara (JP); Hiroaki Kozawa, Omihachiman (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 160 days.

(21) Appl. No.: 14/917,364

(22) PCT Filed: Sep. 9, 2013

(86) PCT No.: PCT/JP2013/074290
§ 371 (c)(1),
(2) Date: Mar. 8, 2016

(87) PCT Pub. No.: WO2015/033478
PCT Pub. Date: Mar. 12, 2015

(65) Prior Publication Data
US 2016/0224830 A1    Aug. 4, 2016

(51) Int. Cl.
*G06F 11/00*        (2006.01)
*G06K 9/00*         (2006.01)
*G01N 30/86*        (2006.01)

(52) U.S. Cl.
CPC ..... *G06K 9/00516* (2013.01); *G01N 30/8634* (2013.01); *G06K 9/0053* (2013.01)

(58) Field of Classification Search
CPC ................................ G06K 9/00516
See application file for complete search history.

(56) References Cited

U.S. PATENT DOCUMENTS

| | | | |
|---|---|---|---|
| 6,415,232 B1 * | 7/2002 | Hayashi | G01N 27/44717 436/161 |
| 2012/0298859 A1 * | 11/2012 | Tanji | H01J 49/0036 250/282 |

OTHER PUBLICATIONS

Written Opinion for PCT/JP2013/074290 dated Dec. 10, 2013. [PCT/ISA/237].
"Piiku Hakei Shori Wo Kakunin Shimashou (Check that the waveform processing is OK)", Shimadzu Corporation, [accessed on Jun. 7, 2013], the Internet <URL: http://www.an.shimadzu.co.jp/hplc/support/lib/lctalk/23/23lab.htm>, 3 pgs.
(Continued)

*Primary Examiner* — Phuong Huynh
(74) *Attorney, Agent, or Firm* — Sughrue Mion, PLLC

(57) ABSTRACT

For a signal waveform to be processed, the continuous wavelet transform is performed with various scale factors, and a wavelet coefficient at each point in time is calculated. On an image showing the strength of the wavelet coefficient with respect to the scale factor and time, ridge lines are detected, and based on these ridge lines, positive and negative peak candidates are extracted, after which an error in the position and width of the peak due to the influence of a neighboring peak is corrected. Subsequently, the degree of non-symmetry of the peak shape or other features are examined to remove false negative peaks due to negative peak artifacts. Subsequently, a true peak cluster, a false peak cluster resulting from the removal of high-frequency components of a high-frequency noise or other causes, and other kinds of peaks are identified, and the obtained result is used to remove false peaks.

28 Claims, 5 Drawing Sheets

(56) References Cited

OTHER PUBLICATIONS

Pan Du, et al., "Improved peak detection in mass spectrum by incorporating continuous wavelet transform-based pattern matching", Bioinformatics, 2006, pp. 2059-2065, vol. 22, No. 17.
"Wavelet Toolbox Gaisetsu Sho (Wavelet Toolbox Quick Guide)", The MathWorks Inc., [accessed on Jun. 18, 2013], the Internet <URL: http://www.mathworks.com/tagteam/58032_TT031_Wavelet_Tlbx _Manual.pdf>, 50 pgs.
International Search Report for PCT/JP2013/074290 dated Dec. 10, 2013 [PCT/ISA/210].

* cited by examiner

PEAK DETECTION METHOD

CROSS REFERENCE TO RELATED APPLICATIONS

This application is a National Stage of International Application No. PCT/JP2013/074290, filed on Sep. 9, 2013, the contents of all of which are incorporated herein by reference in their entirety.

TECHNICAL FIELD

The present invention relates to a peak detection method for detecting a peak which appears on a signal waveform, such as a chromatogram obtained by a chromatographic analysis or a profile spectrum obtained by a mass spectrometry.

BACKGROUND ART

On a chromatogram obtained by a chromatographic analysis, such as a gas chromatography or liquid chromatography, a peak corresponding to a component contained in a sample appears. Normally, the position (time) where the peak appears depends on the kind of compound, while the size of the peak (i.e. its height or area) depends on the amount or concentration of the component corresponding to the peak. Therefore, in order to identify a component in a sample by using a chromatogram, it is important to accurately determine the position of the peak. Similarly, in order to comprehend the amount or concentration of a component in a sample, it is important to accurately determine the height or area of the peak. In any cases, to determine the position of a peak on a chromatogram as well as the height or area value of the peak, it is necessary to correctly detect a significant peak originating from a component based on the waveform of the chromatogram.

In many conventionally and commonly used techniques for detecting a peak on a chromatogram, the tangential inclination of the chromatogram waveform is used as the reference, as in the case of the method described in Non Patent Literature 1. However, such a method has the problem that it is difficult to correctly detect a peak if there is a change in the baseline (as shown in FIG. 5A) or if a considerable amount of noise is superposed (as shown in FIG. 5B). Needless to say, the influence of the baseline change or that of the noise can to some extent be removed by performing a pre-process before the peak detection, such as the baseline correction or the smoothing process for noise removal. However, such a process does not always produce a satisfactory effect.

The tangential inclination of the chromatogram waveform for determining a true peak depends on the width of the peak. Therefore, in order to correctly detect a peak, it is necessary to set the peak detection parameters (e.g. the threshold of the inclination used as the criterion for determination) for each sample. However, in the case of a metabolic analysis, a biomarker search or similar analysis in which a considerable number of samples need to be almost continuously analyzed, it is difficult to set the peak detection parameters for each sample, which means that it is difficult to equally improve the accuracy of the peak detection for a variety of samples.

As a peak detection method which is entirely different from the conventional method and one which can solve the aforementioned problems, a method which uses a ridge line in a wavelet coefficient space has been proposed (see Non Patent Literature 2; this method is hereinafter called the "wavelet ridge line detection method"). The wavelet ridge line detection method is hereinafter briefly described.

In the wavelet ridge line detection method, on raw spectrum data (profile spectrum data) obtained by a mass spectrometry, a continuous wavelet transform is directly performed. i.e. without performing the preprocessing for the baseline correction or noise removal. The wavelet coefficients are determined while a scale factor is varied. The scale factor is one of the two parameters used in transforming the mother wavelet into a wavelet function. It is a parameter for scaling the mother wavelet. In general, the wavelet coefficient relatively shows the extent to which the component of the wavelet function given under specific parameters (e.g. the scale factor) is contained in the original waveform of the signal. In the wavelet ridge line detection method, for each mass-to-charge ratio, the wavelet coefficient is calculated while the scale factor is changed. The calculated result is visualized in a three-dimensional coefficient space with the horizontal axis indicating the mass-to-charge ratio, the vertical axis indicating the scale factor, and the third axis orthogonal to both of the horizontal and vertical axes indicating the strength of the wavelet coefficient. In the visualized image, a characteristic ridge line which shows a local maximum is observed at the position corresponding to a true peak formed on the waveform of the original profile spectrum. This ridge line is utilized to detect the peak on the waveform of the profile spectrum.

The baseline change of the waveform of the profile spectrum over a narrow range of time can be regarded as an odd function. Therefore, by using an even function as the mother wavelet, the odd-function component due to the baseline change can be cancelled out, making it possible to correctly detect a peak without performing the baseline correction beforehand. Another characteristic of this method is that the peaks having various peak widths can be correctly detected by performing a comparative evaluation of the strengths of the wavelet coefficients obtained by using the wavelet functions having various widths produced by changing the scale factor.

The previously described processing, such as the calculation and three-dimensional visualization of the wavelet coefficient by the continuous wavelet transform as well as the display of the ridge line showing a plot of the maximum value of the wavelet coefficient, can be performed by using an existing software program, such as the one described in Non Patent Literature 3.

CITATION LIST

Non Patent Literature

Non Patent Literature 1: "Piiku Hakei Shori Wo Kakunin Shimashou (Check that the waveform processing is OK)", Shimadzu Corporation, [accessed on Jun. 7, 2013], the Internet Non Patent Literature 2: Pan Du, and two other authors, "Improved peak detection in mass spectrum by incorporating continuous wavelet transform-based pattern matching", Bioinformatics, 2006, Vol. 22, No. 17, pp. 2059-2065

Non Patent Literature 3: "Wavelet Toolbox Gaisetsu Sho (Wavelet Toolbox Quick Guide)", The MathWorks Inc., [accessed on Jun. 18, 2013], the Internet

SUMMARY OF INVENTION

Technical Problem

However, according to a study by the present inventors, the conventionally proposed wavelet ridge line detection method has the following problems:

(1) In the conventional wavelet ridge line detection method, it is assumed that a signal waveform on which only a positive peak appears is to be processed. However, depending on the type of the detector used in the chromatograph apparatus, it is often the case that a negative peak appears on the chromatogram. A possible measure for dealing with such a negative peak is to simply handle a negative ridge line. However, negative ridge lines can also occur near the base portion of a normal positive peak. Such a "false" negative peak cannot be distinguished from the "true" negative peak by the simple handling of the negative ridge line.

(2) If there are two peaks neighboring each other, and particularly, if the base portion of one peak is significantly overlapped with that of the other peak, those neighboring peaks simultaneously affect the wavelet coefficient, causing the ridge line corresponding to one peak to be biased toward the ridge line corresponding to the other peak which has a larger breadth and higher signal intensity. Therefore, the position of the peak top estimated from the ridge line may possibly be displaced from the actual position of the peak. FIG. 6 shows such an example. In this case, the peak top position estimated from the ridge line is located at time t2, whereas the actual peak top position is located at time t1. With a glance at the chromatogram, the analysis operator can understand that the peak top is incorrectly detected at a position that is evidently displaced from the peak.

(3) To improve the peak detection performance, it is necessary to separate peaks from noise. In the conventional wavelet ridge line method, the removal of the noise by setting a threshold for judging the peak width, and the removal of the noise using SN ratios are proposed. However, in the case of a chromatograph apparatus, it is often the case that the detection signals outputted from the apparatus are already finished with a low-pass filtering process. When the aforementioned noise estimation techniques are applied to such a signal waveform, it is difficult to distinguish between the case where a peak is present among the noise components as shown in FIG. 5B and the case where a considerable number of true peaks appear as shown in FIG. 5C.

The present invention has been developed to solve such problems. Its objective is to provide a peak detection method which eliminates the previously described drawbacks of the conventional wavelet ridge line detection method and thereby enables the correct detection of a peak on a given signal waveform.

Solution to Problem

The first aspect of the present invention developed for solving the previously described problem is a peak detection method for detecting a peak on a signal waveform showing a change of a signal intensity along a first dimension, the method including:

a) a peak candidate extraction step, in which a continuous wavelet transform is performed on the signal waveform, a wavelet coefficient with a scale factor changed within a predetermined range is determined for each value of the first dimension, and the candidates of the positive and negative peaks appearing on the signal waveform are extracted based on a ridge line which appears in a wavelet coefficient image visualized within a three-dimensional space with the strength of the wavelet coefficient as the third dimension:

b) a false negative peak removal step, in which a false negative peak is identified and removed from the negative peak candidates extracted in the peak candidate extraction step, based on at least either a judgment on the degree of inclination of the negative peak with reference to a baseline estimated from the negative peak candidates, or a judgment on whether or not positive peak candidates are present on both sides of the negative peak concerned.

The second aspect of the present invention developed for solving the previously described problem is a peak detection method for detecting a peak on a signal waveform showing a change of a signal intensity along a first dimension, the method including:

a) a peak candidate extraction step, in which a continuous wavelet transform is performed on the signal waveform, a wavelet coefficient with a scale factor changed within a predetermined range is determined for each value of the first dimension, and the candidates of the positive and negative peaks appearing on the signal waveform are extracted based on a ridge line which appears in a wavelet coefficient image visualized within a three-dimensional space with the strength of the wavelet coefficient as the third dimension;

b) a false peak removal step, in which, for a peak candidate extracted in the peak candidate extraction step, the coefficient of correlation between a waveform obtained by creating an even function simulating the signal waveform at the peak top of the peak candidate and a previously defined model waveform is calculated, a false peak is identified based on the coefficient of correlation, and the false peak is removed from the peak candidates.

In the peak detection method according to the present invention, the signal waveform to be processed is typically a chromatogram obtained by various kinds of chromatograph apparatuses. In this case, the first dimension is time (retention time). The signal waveform to be processed may also be a profile spectrum obtained with a mass spectrometer. In this case, the first dimension is the mass-to-charge ratio. Furthermore, the signal waveform to be processed may also be an absorption spectrum or reflection spectrum obtained with a spectrophotometer or similar device. In this case, the first dimension is the wavelength or wavenumber. Needless to say, signal waveforms other than these examples are also conceivable.

In the peak candidate extraction step of the peak detection method according to the present invention, peak candidates for a given signal waveform are extracted by a technique which is basically the same as described in Non Patent Literature 2, i.e. by the wavelet ridge line detection method. However, as opposed to the conventional wavelet ridge line detection method in which only positive peaks are extracted, the peak detection method according to the present invention is configured to additionally extract candidates of the negative peaks by a similar technique to the one applied to the positive peaks.

In the wavelet ridge line detection method described in Non Patent Literature 2, the "Mexican Hat" wavelet is selected as the mother wavelet used for the continuous wavelet transform. However, in the peak detection method according to the present invention, a normalized single-peak convex function should preferably be used as the mother wavelet. Specifically, a mother wavelet having a wavelength whose base portion is less precisely formed than the portion around the peak top, such as a waveform having the shape of a Gauss function whose breadth is curtailed to approximately two times the standard deviation σ. Such a mother wavelet has no negative portion, and therefore, can advantageously prevent the occurrence of an artifact of the negative peak associated with the continuous wavelet transform.

After both positive and negative peak candidates have been extracted by the peak candidate extraction step, the false peaks due to the peak artifact should be removed from the peak candidates. The technique used for this process is different between the first and second aspects: In the case of the first aspect, only the negative peaks are examined in the false negative peak removal step so as to identify a false negative peak by making at least either a judgment on the degree of inclination of the negative peak with reference to a baseline estimated from the negative peak candidates, or a judgment on whether or not positive peak candidates are present on both sides of the negative peak concerned.

For example, if the degree of inclination of a negative peak exceeds a specific threshold, the peak is considered to be a false negative peak which occurs due to a large inclination of the baseline at the base portion of a positive peak. Besides, as already noted, for example, in the case of a chromatograph apparatus, a negative peak may appear on the chromatogram depending on the type of the detector. Actually, the occurrence frequency of the negative peaks is considerably lower than that of the positive peaks. Therefore, for example, if there is a negative peak with positive peak candidates closely located on both sides, i.e. if a negative peak candidate is sandwiched between two positive peak candidates, the negative peak is considered to be a false negative peak which is actually a pseudo negative peak formed between the two positive peak candidates.

In the second aspect, one or both of the positive and negative peaks are examined in the false peak removal step, in which the coefficient of correlation between a waveform obtained by creating an even function simulating the original signal waveform at the peak top of the peak candidate and a previously defined model waveform (this coefficient is hereinafter called the "even function correlation coefficient") is calculated, and a false peak is identified based on this even function correlation coefficient. For example, an appropriate Gauss function can be used as the model peak waveform. Consider the case where a false peak candidate has occurred due to an inclination of the baseline in the previously described manner. If an even function which simulates a waveform centered on the peak top of this peak candidate on the signal waveform is created, its base portion will be extreme heavy-tailed or noticeably undulated up and down. Consequently, the even function correlation coefficient will be low. Therefore, if the even function correlation coefficient is equal to or lower than a predetermined threshold, the peak can be considered as a false peak. By contrast, in the case where a true peak is present on an inclined baseline, the symmetrical components in the peak are extracted as a result of the even-function creation process. Normally, the waveform after the extracting process is close to a Gauss function and thereby has a high level of correlation with a Gauss (or similar) function. In the present invention, the even function correlation coefficient is used for the judgment on the artifact which occurs due to the previously described problem, and additionally, it is also used as a feature quantity representing the likelihood of the peak.

As described thus far, in the peak detection method according to the present invention, not only the positive peaks but also the negative peaks are detected on the basis of the ridge lines which appear on a three-dimensional display of the wavelet coefficient, after which the false candidates of the peaks are correctly removed. Consequently, the positive and negative peaks appearing on a chromatogram or similar signal waveform are correctly detected.

The peak detection method according to the present invention may preferably further include an SN-ratio-based false peak removal step, in which the signal waveform is divided into a plurality of sections based on a predetermined feature quantity of the signal waveform, and a false peak is identified and removed based on the SN ratio of the signal calculated for each of the sections. Alternatively, the peak detection method according to the present invention may preferably further include a peak-width-based false peak removal step, in which a peak-width distribution of the peak candidates is determined, and a peak having a peak width deviating from that distribution is identified as a false peak.

By these peak detection methods, for example, even in the first aspect, not only the false negative peaks but also the false positive peaks can be correctly removed. Additionally, in both of the first and second aspects, the probability of completely removing a false peak which has not been removed by the previously described method is increased.

The peak detection method according to the present invention may preferably further include a peak position correction step, in which an estimated position of the peak candidate determined in the peak candidate extraction step is corrected based on the signal values on both sides of the estimated position on the signal waveform. Alternatively, the method may preferably further include a peak position correction step, in which an estimated position of the peak candidate determined in the peak candidate extraction step is corrected based on the second derivative values of the signal value on both sides of the estimated position on the signal waveform. In addition to the peak position, the peak width may also be corrected; i.e. the method may preferably further include a peak width correction step, in which the peak width is corrected based on the magnitude of the wavelet coefficient at the position corrected in the peak position correction step.

That is to say, for a given peak candidate, the peak width and peak position are adjusted so as to maximize the degree of matching with the previously defined model peak under the constraint that the adjusted width and position should respectively be within the vicinity of the window size (i.e. peak width) and peak position (e.g. time) based on the scale factor obtained from the ridge line, or more specifically, under the constraint that the peak candidate should be within a predetermined vicinity of the initially estimated peak in terms of both the peak width and peak position. For example, on the signal waveform, if the signal intensity at a position on the right or left side of the initially estimated peak position is higher than the signal intensity at this peak position, the peak position is shifted toward that side by a predetermined amount, and the peak width is determined from the scale factor giving the largest wavelet coefficient at that position. When the strength of the wavelet coefficient has converged on a considerably high value, the peak width and peak position at that point in time can be adopted as the peak width and peak position of the peak candidate.

Consequently, for example, even when there are two mutually neighboring peaks whose base portions overlap each other, the influence of the waveform of one peak on the wavelet coefficient in the other peak is eliminated, so that the width and position of each peak can be correctly determined.

In the peak detection method according to the present invention, it is preferable that:

the method further includes a peak type determination step, in which, for one peak candidate of interest among the peak candidates located in the peak candidate extraction step, whether the peak candidate of interest is a peak in a noise waveform finished with a low-pass filtering process or a peak in a peak-cluster waveform including a plurality of true peaks is determined based on a feature-quantity distribution of a plurality of peak candidates located within a predetermined range centering on the peak candidate of interest; and the threshold for identifying a false peak is changed based on a determination result obtained in the peak type determination step.

Alternatively, the peak type determination step may be performed for each peak candidate in such a manner that whether the peak candidate is a peak in a noise waveform finished with a low-pass filtering process or a peak in a peak-cluster waveform including a plurality of true peaks is determined based on a feature-quantity distribution of all the peak candidates located by the peak candidate extraction step instead of the feature-quantity distribution of a portion of the peak candidates.

As the "feature quantity" in the present context, for example, the probability (extent) of the overlapping of the base portion of one peak with that of another peak, the density of the peaks, or a histogram of the even function correlation coefficient showing the degree of matching between the peak and the model peak waveform can be used. In the case where the SN-ratio-based false peak removal step is provided, the proportion of the peaks which have been removed based on the SN ratio in the SN-ratio-based false peak removal step may be used as the "feature quantity".

As already noted, some types of chromatograph apparatuses are configured to output a signal waveform (chromatogram) obtained by performing a low-pass filtering process on the detection signal. In such a low-pass filtered waveform, the feature quantity of the noise peaks tends to fall within a predetermined range. Therefore, whether a peak candidate is a peak in a noise waveform finished with a low-pass filtering process or a peak in a peak-cluster waveform including a plurality of true peaks can be determined, with a considerable level of correctness, based on the feature-quantity distribution of all peak candidates or that of a plurality of peak candidates located within a predetermined range.

By this technique, for example, a peak-like waveform which may result from a low-pass filtering process performed on white noise can be distinguished from true peaks. As a result, the peak detection accuracy improves.

Advantageous Effects of the Invention

By the peak detection method according to the present invention, the negative peaks which cannot be handled by the conventional wavelet ridge line detection method can be correctly detected. The peaks can be accurately detected even when there are a plurality of peaks located close to each other or when the signal waveform has a seemingly peak-like portion which actually has resulted from a low-pass filtering process performed on white noise.

BRIEF DESCRIPTION OF DRAWINGS

FIG. 5A shows an example with a peak present on a changing baseline, FIG. 5B shows an example with one peak present among noise components, and FIG. 5C shows an example with peaks present in a peak cluster.

DESCRIPTION OF EMBODIMENTS

One example of the peak detection method according to the present invention is hereinafter described with reference to the attached drawings.

Figure 1:
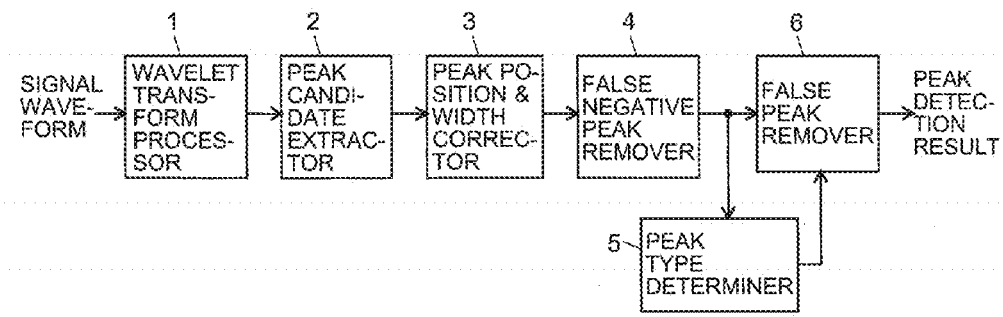
FIG. 1 is a block configuration diagram showing one embodiment of the peak detection system which carries out a peak detection method according to the present invention.
Figure 2:
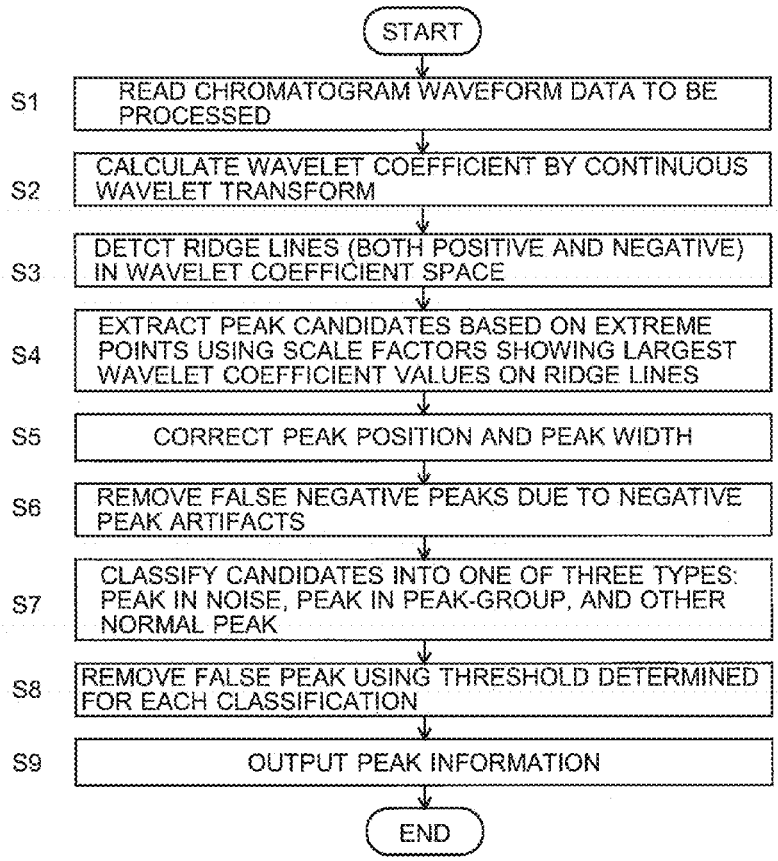
FIG. 2 is a flowchart showing the process flow of the peak detection method carried out by the peak detection system of the present embodiment.

FIG. 1 is a block configuration diagram showing one embodiment of the peak detection system which carries out a peak detection method according to the present invention. FIG. 2 is a flowchart showing the process flow of the peak detection method carried out by the same system.

As shown in FIG. 1, the peak detection system of the present embodiment includes a wavelet transform processor 1 which receives a signal waveform to be processed, a peak candidate extractor 2, a peak position and width corrector 3, a false negative peak remover 4, a peak type determiner 5 and a false peak remover 6. By this system, information on the peaks detected on the signal waveform is outputted.

In the present example, the signal waveform to be processed for the peak detection is a chromatogram waveform obtained with a commonly used liquid chromatograph, gas chromatograph, liquid chromatograph mass spectrometer, gas chromatograph mass spectrometer or similar apparatus. However, the peak detection method according to the present invention is also applicable to signal waveforms other than chromatograms. For example, the signal waveform may be a profile spectrum obtained with a mass spectrometer as well as an absorption spectrum or reflection spectrum obtained with a spectrophotometer.

The peak detection system of the present embodiment can generally be categorized as a data processing system for performing the real-time or batch processing of data collected with a chromatograph apparatus. In most cases, it is realized by using a personal computer as hardware resources and executing, on this computer, a dedicated data processing software program previously installed on the same computer.

According to the flowchart shown in FIG. 2, a peak-detecting operation in the peak detection system of the present embodiment is now described.

The peak detection system of the present embodiment reads chromatogram data to be processed from a (not shown) storage device (Step S1), performs a continuous wavelet transform on the data, and calculates the wavelet coefficient at each point in time while changing the scale factor over a predetermined range as well as in predetermined steps (Step S2).

With f(t) representing a chromatogram whose signal intensity changes depending on time t, and ψ(t) representing the mother wavelet for the continuous wavelet transform, the continuous wavelet transform can be defined by the following equation (1):

$$C(a,b)=\int f(t)\psi((t-b)/a)dt \quad (1)$$

where C is the wavelet coefficient, which is obtained in the form of a function of scale factor a and shift coefficient b. The symbol ∫ means the integration over the entire range of time to be processed, i.e. from the beginning to the ending point of the chromatogram. It should be noted that equation (1) is a generally known definition of the continuous wavelet transform and not a specific matter to the present invention.

Figure 4:
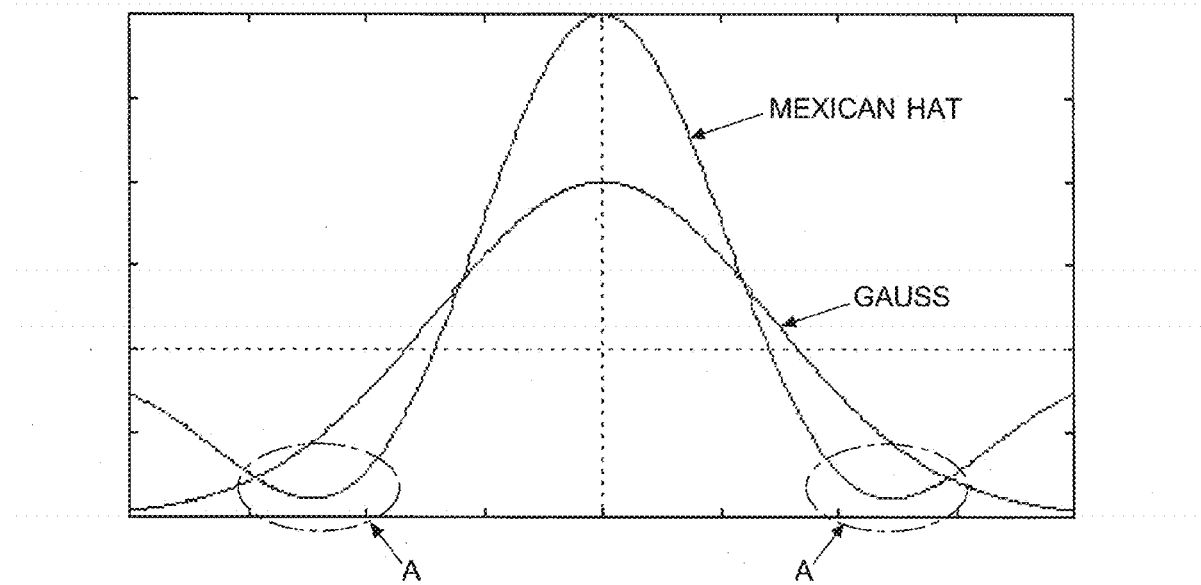
FIG. 4 shows the frequency characteristics of the mother wavelet used in the calculation of the wavelet coefficient.
Figure 5A:
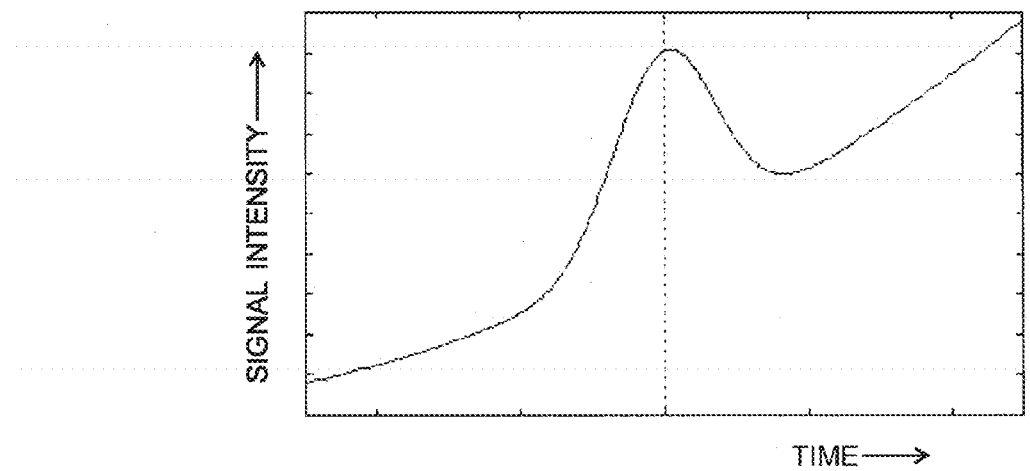
FIGS. 5A-5C are examples of the chromatogram showing various situations of the peak, where
Figure 5B:
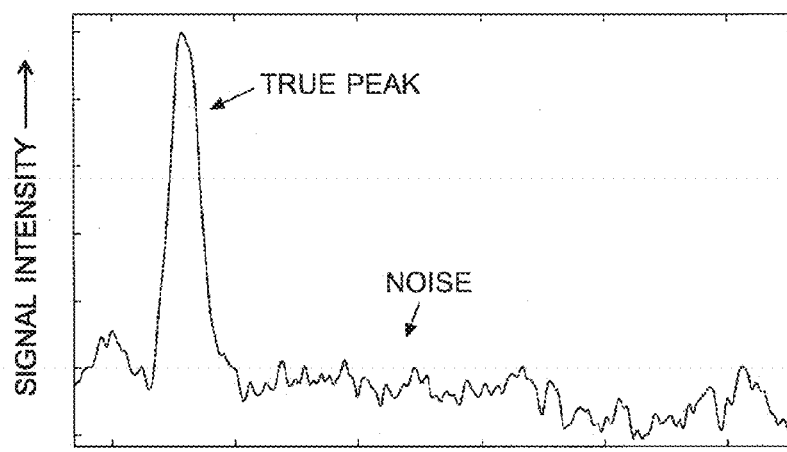
Figure 5C:
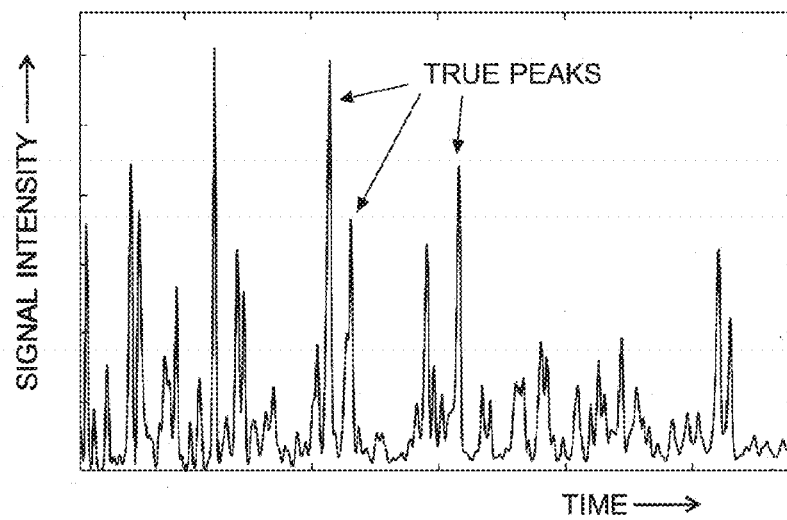

In the method described in the aforementioned Non Patent Literature 2, a function called the "Mexican Hat" which has frequency characteristics as shown in FIG. 4 is used as the mother wavelet ψ(t). By contrast, in the peak detection method of the present embodiment, a Gauss function as shown in FIG. 4 is used as the mother wavelet ψ(t). It should be noted that the function used in the present embodiment is not completely Gaussian but has a waveform obtained by curtailing a Gauss function to a range of 2σ, i.e. two times the standard deviation σ. A non-Gaussian function may also be used as long as it is a single-peak convex function.

As can be understood from FIG. 4, the frequency characteristics of the Mexican Hat have "negative" portion (labelled "A" in FIG. 4), i.e. the section in which the intensity level is lower than the levels on both sides. Therefore, in the case where the Mexican Hat is used as the mother wavelet ψ(t), if an extremely high positive peak is multiplied by this negative portion of the Mexican Hat, an artifact which seems to be a negative peak ("negative peak artifact") occurs on the wavelet coefficient. In the case of the conventional wavelet ridge line detection method, in which negative peaks are not considered in the first place, the occurrence of the negative peak artifact poses no problem. By contrast, in the case of the peak detection method of the present embodiment, in which both positive and negative peaks are to be detected, a serious problem occurs if false peaks due to the negative peak artifact cannot be distinguished from true negative peaks. To address this problem, in the peak detection method of the present embodiment, a Gauss function which has no negative portion is used as the mother wavelet ψ(t), whereby the occurrence of the negative peak artifact due to the wavelet transform can be avoided.

To perform the previously described wavelet transform, for example, the "Wavelet tool box" described in Non Patent Literature 3 can be used. In this case, for example, after the mother wavelet and the range of the scale factor are specified, the continuous wavelet transform on the target chromatogram data is executed, whereby a three-dimensional image is obtained within a coefficient space in which the strength of the wavelet coefficient is represented by colored presentations on a two-dimensional graph with the abscissa axis indicating time (shift coefficient) and the coordinate axis indicating the scale factor.

Next, the peak candidate extractor 2 extracts candidates of the positive and negative peaks by detecting ridge lines on the three-dimensional display of the wavelet coefficient, as well as determines the initial values of the position (time) and peak width of each peak candidate (Steps S3 and S4). As the method for detecting the ridge lines in the three-dimensional display of the wavelet coefficient, the method described in Non Patent Literature 2 is simply expanded toward both positive and negative sides. That is to say, a positive peak candidate is located based on a ridge line which sequentially traces the maximum values starting from the wavelet coefficient corresponding to a large scale factor (i.e. low frequency). Similarly, a negative peak candidate is extracted based on a ridge line which sequentially traces the minimum values. Usually, a number of peak candidates are thereby extracted.

Figure 6:
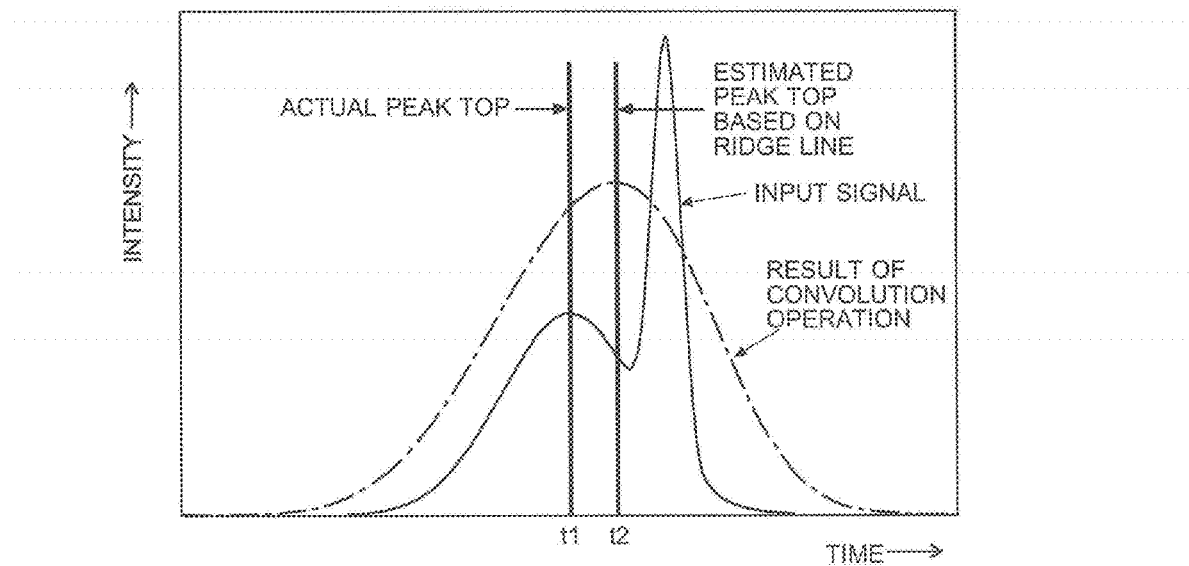
FIG. 6 shows an example of the case where the position of the extreme point of the wavelet coefficient is displaced due to the influence of a neighboring peak.

In ideal situations, the ridge line based on the wavelet coefficients should indicate the position (in the present case, the point in time) of the peak center (peak top). However, when a plurality of peaks are located close to each other, the wavelet coefficient components due to the closely located peaks are added, with the result that the position of the extreme point of the wavelet coefficient is displaced from the actual position of the peak center, causing a displacement of the peak position as shown in FIG. 6. In the wavelet ridge line detection method described in Non Patent Literature 2, the biasing effect of the neighboring peak on the extreme point is minimized by defining, as the peak center, the position at which the extreme point with the smallest scale factor (i.e. the smallest peak width) is located among the plurality of peak positions detected as the ridge lines. However, by such a method, the peak position cannot be correctly estimated if high-frequency noise is superimposed.

Accordingly, in the peak detection method of the present embodiment, the scale factor which gives the largest wavelet coefficient on the ridge line is adopted in order to determine the peak position in a more stable manner even when high-frequency noise is present. In other words, a scale factor which gives a wavelet function having the same width as the peak in ideal situations is adopted. By this method, if the peak is a single peak, the peak position can be determined with a higher level of accuracy and stability than in the case of using a wavelet function with a higher frequency. However, as noted earlier, the ridge line may be subject to the biasing effect due to the neighboring peak. Therefore, after the peak candidates are located as well as the initial values of the peak position and peak width of each peak candidate are determined, the peak position and width corrector 3 corrects the peak position and peak width of each peak candidate by the following procedure (Step S5).

Figure 3:
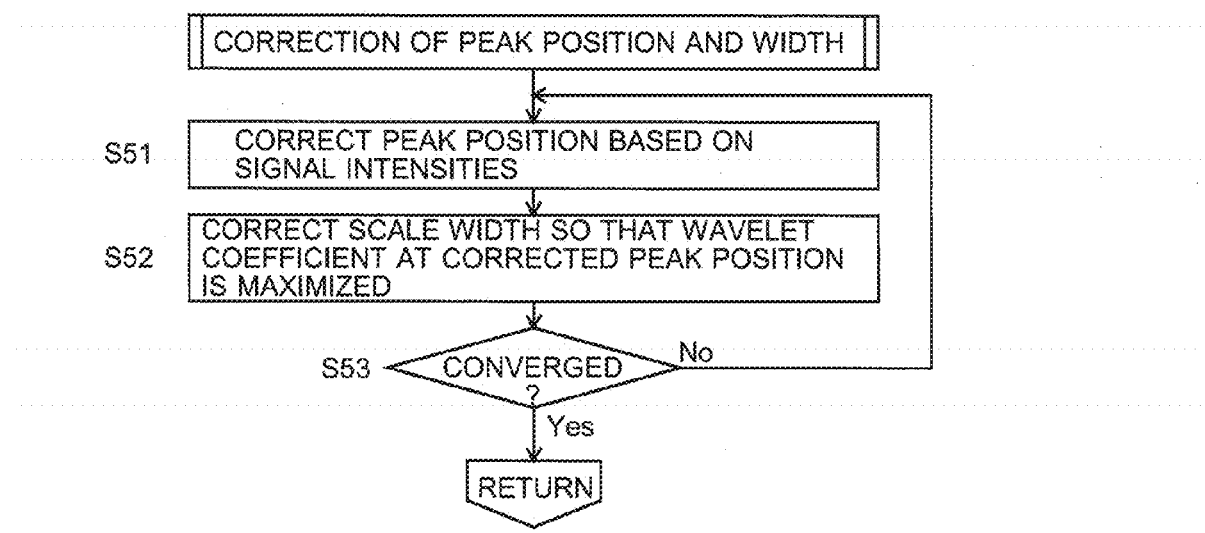
FIG. 3 is a flowchart showing the subroutine for the correction of the peak position and peak width in FIG. 2.

FIG. 3 is a flowchart showing the subroutine for the process of Step S5 in FIG. 2.

For one peak candidate, after the initial position is given, the peak position is corrected with reference to the signal intensities on both sides of the initial position on the chromatogram waveform (Step S51), i.e. if the peak is positive, the peak position is shifted by a predetermined distance in the direction in which the signal intensity increases (or if the peak is negative, the shift is made in the opposite direction in which the signal intensity decreases). For example, in the case of FIG. 6, if t2 is the initial position, the signal intensity on the earlier side from the initial position is higher than on the later side. Accordingly, the peak position is corrected so as to shift it toward the earlier side.

If the baseline is extremely inclined, the signal intensity at one end of the peak may possibly be the highest (i.e. higher than the signal intensity at the peak top). In such a case, the previously described method which depends on the signal intensities cannot be used. To address this problem, it is preferable to impose the restriction that the peak-position correction should not be performed if the position after the peak-position correction is considered to be abnormally distant on the basis of the initially estimated position and the peak width, or specifically, for example, if the position after the peak-position correction is farther than the predetermined position calculated from the initially estimated position and the peak width. In this case, it is preferable to additionally impose the restriction that a correction which causes the peak position to reach beyond an inflection point of the signal waveform located by using the second derivative of this waveform should not be performed.

Next, at the peak position after the correction, the peak width is corrected so that the peak width becomes equal to the scale factor which gives the largest wavelet coefficient (Step S52). However, in practice, a pump noise due to the pulsation of the liquid-sending pump in the liquid chromatograph may be superimposed on the peak, or the peak may be superposed on a significantly changing baseline. Therefore, instead of simply comparing the wavelet coefficients given by the respective scale factors, the wavelet coefficients may be individually and appropriately weighted before being compared to locate the largest scale factor. After the peak position and peak width are corrected, whether or not the peak position and peak width have been sufficiently corrected to a certain extent is determined by examining, for example, whether or not the rate of change in the signal intensity has converged to a certain range or whether or not the rate of change in the peak width has been equal to or lower than a certain threshold (Step S53). If the correction is insufficient, the operation returns to Step S51 to repeat the processes of Steps S51 and S52. If it is concluded that the peak position and peak width have been sufficiently corrected to a certain extent, the correction is discontinued.

Usually, the peak candidates extracted in Step S4 include a considerable number of false peaks which are not actual peaks. Accordingly, the false negative peak remover 4 initially removes false negative peaks due to the negative peak artifact (Step S6).

Figure 8:
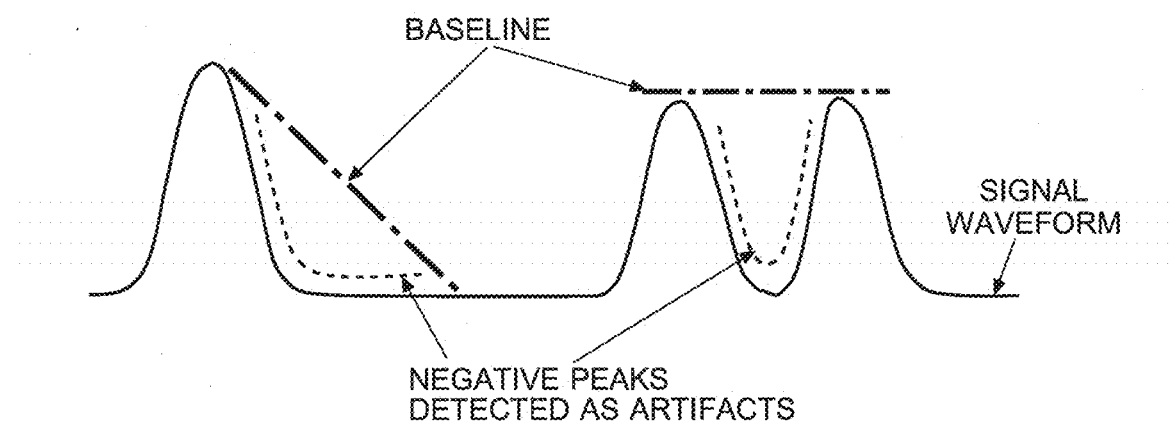
FIG. 8 shows an example in which an artifact of a negative peak occurs in a chromatogram.

In normal situations, the negative peak artifact occurs in the base portion of a positive peak or in the trough between one positive peak and another, as shown in FIG. 8. The example in the left area of FIG. 8 is the case where the presence of a steeply inclined baseline has been falsely recognized due to the presence of a positive peak, with the result that the base portion of this positive peak has been recognized as a negative peak bulging downward from the baseline. The example in the right area of FIG. 8 is the case where the presence of two closely located positive peaks with almost equal signal intensities has caused the false recognition of a substantially horizontal baseline located at the peak-top level, with the result that the trough section between the positive peaks has been recognized as a negative peak bulging downward from the baseline.

The false peak due to the negative peak artifact in the left area of FIG. 8 is detected as a peak having a considerably sloped shape relative to the true baseline. Accordingly, the false negative peak remover 4 detects this type of false negative peak by recognizing that the peak is noticeably sloped, or by creating an even function which simulates the peak within a peak-top section on the signal waveform, calculating the coefficient of correlation between the even function and a prepared model peak, and examining the coefficient value. It should be noted that such an examination is also available for detecting false positive peaks as well as false negative peaks. Therefore, the system may be configured to remove false peaks regardless of positive or negative peaks.

Figure 9:
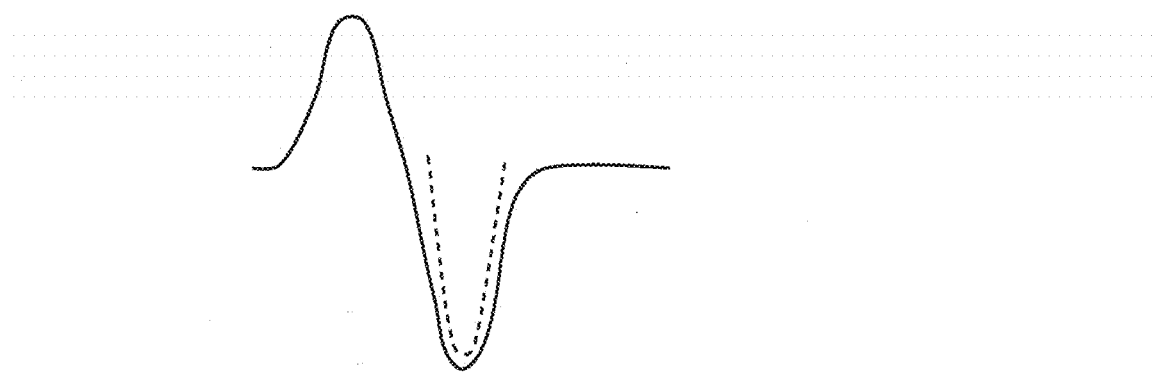
FIG. 9 shows an example in which a negative peak is significantly bulged toward the negative side relative to the baseline of the nearby peak in a chromatogram.

On the other hand, when there are two closely located positive peaks as shown in the right area of FIG. 8, in principle, the peak may possibly be a true negative peak. However, it is common knowledge that a chromatogram is much more likely to have positive peaks occurring on it than negative peaks. Therefore, it is reasonable to directly conclude that the peak is a negative peak artifact. Alternatively, as shown in FIG. 9, the false negative peak remover 4 may detect, as a negative peak, only such a negative peak candidate that protrudes downward with an intensity equal to or greater than a certain amount as compared to the baseline and peak heights of the neighboring peaks, while regarding any negative peak candidate which does not satisfy this condition as a false peak and removing it.

Figure 7:
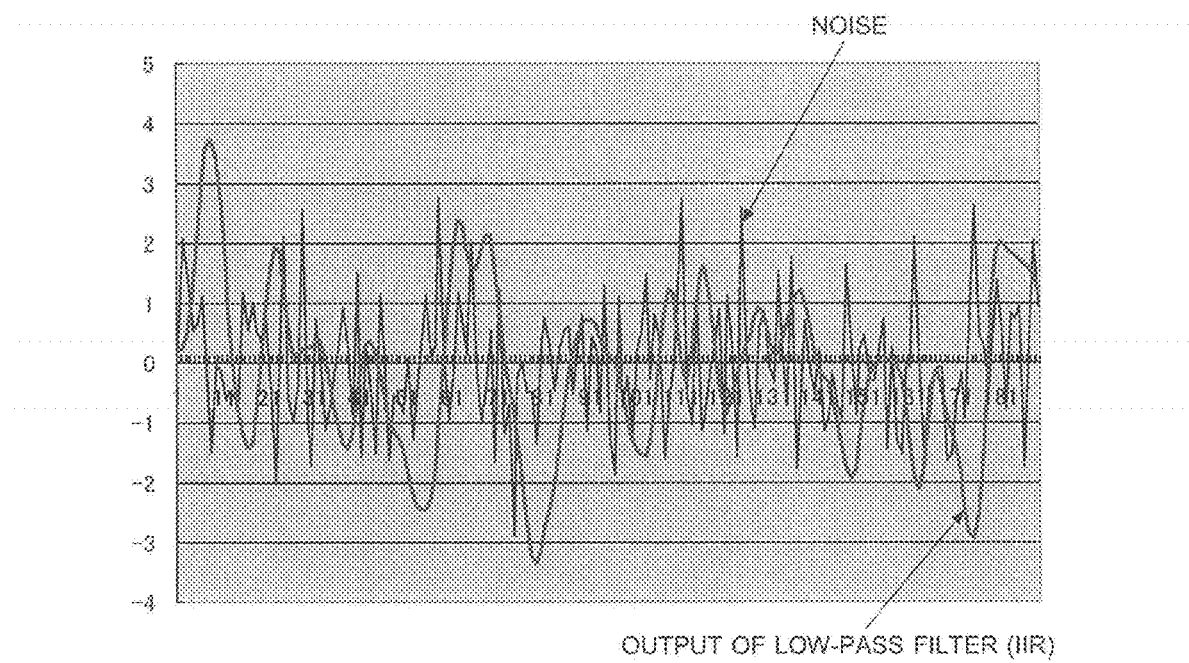
FIG. 7 shows a signal waveform obtained when a low-pass filtering process is performed on white noise.

In the wavelet ridge line detection method described in Non Patent Literature 2, after the ridge line of the wavelet coefficients is detected, its SN ratio is calculated with reference to the signal energy of its high-frequency components to determine whether the peak represented by the ridge line is a true peak or a false peak due to noise. However, some type of chromatograph apparatus used for obtaining data outputs a signal which has already been finished with a low-pass filtering process and therefore contains a reduced amount of high-frequency components. In such a case, a waveform which actually is a high-frequency white noise superposed on a signal waveform appears to be a cluster of a considerable number of peak waveforms, as shown in FIG. 7. Additionally, a signal waveform produced by a chromatograph apparatus may contain other forms of noise superposed on it, such as a pump noise which is difficult to distinguish from peaks or a noise which originates from the fluctuation of a light source in a detector which utilizes an optical technique. Such forms of noise also appear to be a peak cluster. If the conventional wavelet ridge line detection method is applied to such a signal, all of these peaks which are actually noise components will be detected as peaks.

By contrast, in the peak detection system of the present embodiment, the peak type determiner 5 determines whether or not a peak on an inputted signal waveform is a waveform which has resulted from a low-pass filtering process performed on a noise component, as well as whether or not it is a noise component shaped like a peak cluster, such as a pump noise.

In the case of a peak-like waveform resulting from a low-pass filtering process performed on white noise, as well as a pump noise, light-source noise or other peak-like waveforms (i.e. false peak waveforms), a feature quantity of the peak (which will be described later) tends to fall within a certain range. Accordingly, the feature-quantity distribution of the peaks is previously determined on the basis of a signal waveform which is expected to be actually processed. Based on an appropriate threshold set from this distribution, the feature quantity calculated from the signal waveform being processed is examined so as to determine whether a certain range of time within the given signal waveform is a noise section or a peak-cluster section.

The following quantities are available as the feature quantity of the peaks. Any of these feature quantities is most likely to fall within a predetermined range in the case of a false peak cluster which results from the aforementioned kinds of noise, while departing from that range in the case of true peaks which have not originated from any noise.

(1) Probability of Overlapping of One Peak with Another Peak

In the present embodiment, empirically, a section in which this probability is 15% or lower is set as a peak-cluster section, while a section in which this probability is 50% or higher is set as a noise section.

(2) Peak Density (Number of Peaks/Number of Data Points, or Accumulated Value of Peak Width/Number of Data Points)

In the present embodiment, empirically, a section is set as a possible noise section if 80% or more of the section is occupied by peaks.

(3) Histogram of Even Function Correlation Coefficient Showing Degree of Matching in Shape Between Peak and Model Peak In the present embodiment, empirically, a section is set as a possible noise section if the area of the bins having an even function correlation coefficient of approximately 0.7 or higher in the histogram is lower than 20% of the entire area.

(4) Histogram of Peak Height Normalized by High-Frequency Noise Components

In the present embodiment, empirically, a section is set as a possible noise section if the ratio of the height of a low peak which is at a distance of $2\sigma$ or larger from the noise-component distribution and the height of a high peak which is also at a distance of $2\sigma$ or larger from the noise-component distribution is 1:3 or greater.

(5) Density of Inflection Points

In the present embodiment, empirically, if 15 to 70% of the data points within a section corresponding to one wavelength of the high-frequency noise are inflection points, it is considered that the section is most likely to be a noise section.

Needless to say, the aforementioned numerical values used for the noise determination and other purposes are mere examples and may be appropriately changed.

Specifically, the peak type determiner 5 divides the inputted chromatogram waveform into appropriate segments of time in time-series order. For each time segment, it examines at least one of the aforementioned feature quantities of the peak cluster included in the time segment and determines whether or not the feature quantity falls within the preset threshold range, so as to thereby determine whether the section in question is a noise section in which the previously described kind of characteristic noise is present, or a peak-cluster section in which a number of peaks are present, or a section different from any of them (e.g. a section having a noticeably isolated peak with only a small amount of noise). In this manner, each peak candidate extracted from the chromatogram waveform is classified into a peak in a noise, a peak in a peak cluster, or other normal peaks (Step S7).

After the peak candidates are classified, the false peak remover 6 determines, for each peak candidate, whether it is a false peak or true peak, and removes the false peak (Step S8). Specifically, for each of the three kinds of sections (i.e. noise section, peak-cluster section, and section different from any of them), the following feature quantities are calculated from the peak candidates and noise components included in the section, and the false peak is identified based on the thresholds respectively determined for these feature quantities:

(A) A peak-height histogram
(B) A peak-width histogram
(C) A high-frequency noise level
(D) A histogram of the peaks which have been identified as false peaks due to an even function correlation coefficient (the index showing the degree of matching in the waveform shape between a peak and a model peak) and the feature quantities (A)-(D)

The thresholds for examining the feature quantities can be determined as follows: For the histogram as used in (A), (B) or (D), a range over which the peak is presumably distributed can be determined from the histogram shape, and the threshold can be determined so that any peak departing from this range is regarded as a false peak. For the noise level in (C), a level which equals the noise level multiplied by a predetermined number can be used as the threshold, as in the case of a normal false-peak detection based on the SN ratio. For example, in ideal situations, the height of the false peak noise follows a chi-squared ($\chi^2$) distribution. Therefore, an appropriate threshold can be determined by estimating the width of the distribution from the lower-noise end. In this manner, the thresholds for the false-peak identification are set for each of the three kinds of sections. According to those thresholds, whether or not each peak candidate is a false peak is determined.

It should be noted that histograms (A) and (B) should preferably be histograms of the true peaks. The removal of the false peaks increases the probability that the remaining peaks are true peaks, which in turn causes a change of the histogram itself. Simultaneously, histogram (D) also similarly changes. In other words, by using a result in which some of the peak candidates have been identified as false peaks, it is possible to refine the peak-width and peak-height histograms for each of the false and true peaks, i.e. to create more accurate histograms.

Accordingly, it is preferable to once more perform a similar false-peak identification process using the aforementioned histogram information obtained for each of the false and true peaks as additional information, whereby a more accurate false peak identification can be achieved. Specifically, instead of a single false-peak identification process which removes all false peaks, a rough false-peak identification process is initially performed to remove candidates which are most likely to be false peaks. Subsequently, by using the obtained result, the level of accuracy of the same false-peak identification process is enhanced so as to locate peak candidates for which it is difficult to determine whether they are false or true peaks. In this manner, the false peaks can be correctly removed while avoiding the wrong removal of a true peak.

After the false peaks are removed, the information on the remaining peak candidates which are considered to be the true peaks is outputted along with the peak position, peak width and other related information (Step S9).

As described thus far, the peak detection system of the present embodiment can detect peaks more correctly than conventional systems, using the wavelet ridge line detection.

It should be noted that the previous embodiment is a mere example of the present invention, and any change, modification or addition appropriately made within the spirit of the present invention will naturally fall within the scope of claims of the present application.

REFERENCE SIGNS LIST

1 . . . Wavelet Transform Processor
2 . . . Peak Candidate Extractor
3 . . . Peak Position and Width Corrector
4 . . . False Negative Peak Remover
5 . . . Peak Type Determiner
6 . . . False Peak Remover

The invention claimed is:

1. A peak detection method for detecting a peak on a signal waveform showing a change of a signal intensity along a first dimension, comprising:

a) a signal waveform obtaining step, in which the signal waveform is obtained from an analyzer;

b) a peak candidate extraction step performed by a processor of a data processing apparatus, in which a continuous wavelet transform is performed on the signal waveform, a wavelet coefficient with a scale factor changed within a predetermined range is determined for each value of the first dimension, and candidates of positive and negative peaks appearing on the signal waveform are extracted based on a ridge line which appears in a wavelet coefficient image visualized within a three-dimensional space with a strength of the wavelet coefficient as a third dimension;

c) a false negative peak removal step performed by the processor, in which a false negative peak is identified and removed from the negative peak candidates extracted in the peak candidate extraction step, based on at least either a judgment on a degree of inclination of the negative peak with reference to a baseline estimated from the negative peak candidates, or a judgment on whether or not positive peak candidates are present on both sides of the negative peak concerned.

2. A peak detection method for detecting a peak on a signal waveform showing a change of a signal intensity along a first dimension, comprising:

a) a signal waveform obtaining step, in which the signal waveform is obtained from an analyzer;

b) a peak candidate extraction step performed by a processor of a data processing apparatus, in which a continuous wavelet transform is performed on the signal waveform, a wavelet coefficient with a scale factor changed within a predetermined range is determined for each value of the first dimension, and candidates of positive and negative peaks appearing on the signal waveform are extracted based on a ridge line which appears in a wavelet coefficient image visualized within a three-dimensional space with a strength of the wavelet coefficient as a third dimension;

c) a false peak removal step performed by the processor, in which, for a peak candidate extracted in the peak candidate extraction step, a coefficient of correlation between a waveform obtained by creating an even function simulating the signal waveform at a peak top of the peak candidate and a previously defined model waveform is calculated, a false peak is identified based on the coefficient of correlation, and the false peak is removed from the peak candidates.

3. The peak detection method according to claim 1, wherein:

a normalized single-peak convex function is used as a mother wavelet used in the continuous wavelet transform in the peak candidate extraction step.

4. The peak detection method according to claim 1, further comprising:

an SN-ratio-based false peak removal step, in which the signal waveform is divided into a plurality of sections based on a predetermined feature quantity of the signal waveform, and a false peak is identified and removed based on the SN ratio of the signal calculated for each of the sections.

5. The peak detection method according to claim 1, further comprising:

a peak-width-based false peak removal step, in which a peak-width distribution of the peak candidates is determined, and a peak having a peak width deviating from that distribution is identified as a false peak.

6. The peak detection method according to claim 1, further comprising:

a peak position correction step, in which an estimated position of the peak candidate determined in the peak candidate extraction step is corrected based on signal values on both sides of the estimated position on the signal waveform.

7. The peak detection method according to claim 1, further comprising:

a peak position correction step, in which an estimated position of a peak candidate determined in the peak candidate extraction step is corrected based on second derivative values of signal values on both sides of the estimated position on the signal waveform.

8. The peak detection method according to claim 6, further comprising:

a peak width correction step, in which an estimated peak width of a peak candidate determined in the peak candidate extraction step is corrected based on a magnitude of the wavelet coefficient at the position corrected in the peak position correction step.

9. The peak detection method according to claim 1, wherein:

the method further comprises a peak type determination step, in which, for one peak candidate of interest among the peak candidates located in the peak candidate extraction step, whether the peak candidate of interest is a peak in a noise waveform finished with a low-pass filtering process or a peak in a peak-cluster waveform including a plurality of true peaks is determined based on a feature-quantity distribution of a plurality of peak candidates located within a predetermined range centering on the peak candidate of interest; and a threshold for identifying a false peak is changed based on a determination result obtained in the peak type determination step.

10. The peak detection method according to claim 1, wherein:

the method further comprises a peak type determination step, in which, for each peak candidate, whether the peak candidate is a peak in a noise waveform finished with a low-pass filtering process or a peak in a peak-cluster waveform including a plurality of true peaks is determined based on a feature-quantity distribution of all the peak candidates located by the peak candidate extraction step; and a threshold for identifying a false peak is changed based on a determination result obtained in the peak type determination step.

11. The peak detection method according to claim 9, wherein:

an extent of overlapping of one peak with another peak is used as the feature quantity to determine the feature-quantity distribution of the plurality of peak candidates in the peak type determination step.

12. The peak detection method according to claim 9, wherein:

the method further comprises an SN-ratio-based false peak removal step, in which the signal waveform is divided into a plurality of sections based on a predetermined feature quantity of the signal waveform, and a false peak is identified and removed based on the SN ratio of the signal calculated for each of the sections; and a proportion of the peaks removed based on the SN ratio in the SN-ratio-based false peak removal step is used as the feature quantity to determine the feature-quantity distribution of the plurality of peak candidates in the peak type determination step.

13. The peak detection method according to claim 2, wherein:

a normalized single-peak convex function is used as a mother wavelet used in the continuous wavelet transform in the peak candidate extraction step.

14. The peak detection method according to claim 2, further comprising:
an SN-ratio-based false peak removal step, in which the signal waveform is divided into a plurality of sections based on a predetermined feature quantity of the signal waveform, and a false peak is identified and removed based on the SN ratio of the signal calculated for each of the sections.

15. The peak detection method according to claim 2, further comprising:
a peak-width-based false peak removal step, in which a peak-width distribution of the peak candidates is determined, and a peak having a peak width deviating from that distribution is identified as a false peak.

16. The peak detection method according to claim 2, further comprising:
a peak position correction step, in which an estimated position of the peak candidate determined in the peak candidate extraction step is corrected based on signal values on both sides of the estimated position on the signal waveform.

17. The peak detection method according to claim 2, further comprising:
a peak position correction step, in which an estimated position of a peak candidate determined in the peak candidate extraction step is corrected based on second derivative values of signal values on both sides of the estimated position on the signal waveform.

18. The peak detection method according to claim 7, further comprising:
a peak width correction step, in which an estimated peak width of a peak candidate determined in the peak candidate extraction step is corrected based on a magnitude of the wavelet coefficient at the position corrected in the peak position correction step.

19. The peak detection method according to claim 16, further comprising:
a peak width correction step, in which an estimated peak width of a peak candidate determined in the peak candidate extraction step is corrected based on a magnitude of the wavelet coefficient at the position corrected in the peak position correction step.

20. The peak detection method according to claim 17, further comprising:
a peak width correction step, in which an estimated peak width of a peak candidate determined in the peak candidate extraction step is corrected based on a magnitude of the wavelet coefficient at the position corrected in the peak position correction step.

21. The peak detection method according to claim 2, wherein:
the method further comprises a peak type determination step, in which, for one peak candidate of interest among the peak candidates located in the peak candidate extraction step, whether the peak candidate of interest is a peak in a noise waveform finished with a low-pass filtering process or a peak in a peak-cluster waveform including a plurality of true peaks is determined based on a feature-quantity distribution of a plurality of peak candidates located within a predetermined range centering on the peak candidate of interest; and
a threshold for identifying a false peak is changed based on a determination result obtained in the peak type determination step.

22. The peak detection method according to claim 2, wherein:
the method further comprises a peak type determination step, in which, for each peak candidate, whether the peak candidate is a peak in a noise waveform finished with a low-pass filtering process or a peak in a peak-cluster waveform including a plurality of true peaks is determined based on a feature-quantity distribution of all the peak candidates located by the peak candidate extraction step; and
a threshold for identifying a false peak is changed based on a determination result obtained in the peak type determination step.

23. The peak detection method according to claim 21, wherein:
an extent of overlapping of one peak with another peak is used as the feature quantity to determine the feature-quantity distribution of the plurality of peak candidates in the peak type determination step.

24. The peak detection method according to claim 10, wherein:
an extent of overlapping of one peak with another peak is used as the feature quantity to determine the feature-quantity distribution of the plurality of all the peak candidates in the peak type determination step.

25. The peak detection method according to claim 22, wherein:
an extent of overlapping of one peak with another peak is used as the feature quantity to determine the feature-quantity distribution of all the peak candidates in the peak type determination step.

26. The peak detection method according to claim 21, wherein:
the method further comprises an SN-ratio-based false peak removal step, in which the signal waveform is divided into a plurality of sections based on a predetermined feature quantity of the signal waveform, and a false peak is identified and removed based on the SN ratio of the signal calculated for each of the sections; and
a proportion of the peaks removed based on the SN ratio in the SN-ratio-based false peak removal step is used as the feature quantity to determine the feature-quantity distribution of the plurality of peak candidates in the peak type determination step.

27. The peak detection method according to claim 10, wherein:
the method further comprises an SN-ratio-based false peak removal step, in which the signal waveform is divided into a plurality of sections based on a predetermined feature quantity of the signal waveform, and a false peak is identified and removed based on the SN ratio of the signal calculated for each of the sections; and
a proportion of the peaks removed based on the SN ratio in the SN-ratio-based false peak removal step is used as the feature quantity to determine the feature-quantity distribution of all the peak candidates in the peak type determination step.

28. The peak detection method according to claim 22, wherein:
the method further comprises an SN-ratio-based false peak removal step, in which the signal waveform is divided into a plurality of sections based on a predetermined feature quantity of the signal waveform, and a false peak is identified and removed based on the SN ratio of the signal calculated for each of the sections; and a proportion of the peaks removed based on the SN ratio in the SN-ratio-based false peak removal step is used as the feature quantity to determine the feature-quantity distribution of all the peak candidates in the peak type determination step.

\* \* \* \* \*